US005554590A

United States Patent [19]
Fisher et al.

[11] Patent Number: 5,554,590
[45] Date of Patent: Sep. 10, 1996

[54] METHOD OF TREATING ASTHMA

[75] Inventors: Robert H. Fisher; W. James Metzger; Ruth A. Henriksen, all of Greenville, N.C.

[73] Assignee: East Carolina University, Greenville, N.C.

[21] Appl. No.: 932,374

[22] Filed: Aug. 19, 1992

[51] Int. Cl.$^6$ ..................................................... A61K 38/16
[52] U.S. Cl. ................................. 514/8; 514/12; 514/21; 424/85.2; 530/380
[58] Field of Search ................................... 514/12, 8, 21; 424/85.2; 530/380

[56] References Cited

FOREIGN PATENT DOCUMENTS 9201465  2/1992  WIPO .

OTHER PUBLICATIONS

Reddingari et al., Clin. Res., vol. 40(2), p. 228A, Abstract, 1992.
Alam et al., The Faseb Journal, Abstracts, vol. 6 (2), pp. A2005, Feb. 1992. (abstract No. 6188).
Kuna et al., Jour. Allergy & Clin. Immunol., vol. 87 (1), part 1, p. 207 (abstract #272), Jan. 1991.
Brindley, L L et al., J. Clin. Invest., vol. 72, pp. 1218–1223, 1983.
Kuna et al., T. Exp. Med., vol. 175, pp. 489–493, 1992 Feb.
Alam et al., Jour. Allergy & Clin. Immunol., vol. 87(1), part 1, p. 241, 1991.
Alam et al J. Clin. Invest. vol. 82 (Dec. 1988) pp. 2056–2062.
Fisher et al J. Allergy Clin Immunol. vol. 79, p. 196 (1987) Abstract.
Kuna et al., *IL–8 Inhibits Histamine Release from Human Basophils Induced By Histamine–Releasing Factors, Connective Tissue Activating Peptide III, and IL–3*[1], The Journal of Immunology, vol. 147, 1920–1924, No. 6, Sep. 1991.
Alam et al., *Study of the Cellular Origin of Histamine Release Inhibitory Factory Using Highly Purified Subsets of Mononuclear Cells*[1], The Journal of Immunology, Crawley, vol. 143, 2280–2284, No. 7, Oct. 1989.
Alam et al., *Detection of Histamine Release Inhibitory Factor—and Histamine Releasing Factor–like Activities in Bronchoalveolar Lavage Fluids*, AM REV RESPIR DIS 1990; 141:666–671.
Schroder et al., *Lipopolysaccharide–Stimulated Human Monocytes Secrete, Apart From Neutrophil–Activating Peiptide 1/Interleukin 8, A Second Neutrophil–Activating Protein*, J. Exp. Med., vol. 171, Apr. 1990, 1091–1100.

Wolpe et al., *Macrophage Inflammatory Proteins 1 and 2: Members of a Novem Superfamily of Cytokines*, The FASEB Journal, vol. 3, Dec. 1989.
SICA et al., *Mono Chemotactic and Activating Factor Gene Expression Induced In Endothelial Cells By IL–1 and Tumor Necrosis Factor*, The Journal of Immunology, vol. 144, 3034–3038, No. 8, Apr. 15, 1990.
Schall et al., *Selective Attraction of Monocytes and T Lymphocytes of the Memory Phenotype by Cytokine RANTES*, Nature, vol. 347, 18 Oct. 1990.
Mukaida et al., *Regulation of Human Interleukin 8 Gene Expression and Binding of Several Other Members of the Intercrine Family to Receptors for Interleukin–8 Chemotactic Cytokines*, Advances in Exp. Med. & Biol., Plenum Press, pp. 31–38, 1991.
Schall et al., *A Human T Cell–Specific Molecule is a Member of a New Gene Family*, The Journal of Immunology, vol. 141, 1 018–1025, No. 3, Aug. 1, 1988.
Hechtman et al., *Intravascular IL–8, Inhibitor of Polymorphonuclear Leukocyte Accumulation at Sites of Acute Inflammation*, The Journal of Immunology, vol. 147, 883–892, Aug. 1, 1991.
Oppenheim et al., *Properties of the Novel Proinflammatory Supergene "Intercine" Cytokine Family*, Annu. Rev. Immunol. 1991, 9:617–48.
Alam et al., *Effect of 8KD Family of Cytokines on Basophil/Mast Cell Histamine Release: Macrophage Inflammatory Protein–1 (MIP–1) Has Histamine Releasing Activity*, Clinical Research, vol. 40, No. 2, 1992.
Kaplan et al., Int. Arch. Allergy Appl. Immunol., vol. 94, pp. 148–153, 1991.
Baeza et al., J. Clin. Invest., vol. 85, pp. 1516–1521, 1990.
Walz et al., J. Exp. Med., vol. 171, pp. 449–454, 1990.
Kaplan et al., Clin. Exp. Allergy, vol. 21 (Suppl. 1), pp. 8–16, 1991.
Reddingari et al., J. Allergy Clin. Immunol., vol. 87(1), Part 1, #406, 1991.

*Primary Examiner*—Chhaya D. Sayala
*Attorney, Agent, or Firm*—Bell, Seltzer, Park & Gibson

[57] ABSTRACT

A method of treating asthma in a subject in need of such treatment comprises contacting Asthma Reversal Factor to the respiratory epithelium of the subject. The active agent is preferably contacted to the subject's respiratory epithelium by causing the subject to inhale respirable particles comprised of the active agent.

12 Claims, 7 Drawing Sheets

METHOD OF TREATING ASTHMA

This invention was made with government support under grant number NIH 5 RO1 AI26726 from the National Institutes of Health. The government may have certain rights to this invention.

FIELD OF THE INVENTION

This invention generally relates to the treatment of asthma, and particularly relates to the treatment of asthma with Asthma Reversal Factor (ARF) agonists.

BACKGROUND OF THE INVENTION

Hallmarks of asthma include reversible airway obstruction, and non-specific airway hyperresponsiveness. Hyperresponsiveness not only determines the ease with which obstruction will occur, but also closely relates clinically with symptomatology. While the cause of asthma is still unknown, several classes of anti-asthma medications are currently available. Most treat bronchoconstriction, but do not reverse the accompanying hyperresponsiveness. Inhaled steroids can reverse hyperresponsiveness, but this effect can have a slow onset and generally requires at least daily administration of medication.

Evidence indicates that platelets in the peripheral blood are activated in-vivo during allergen induced attacks of asthma, and further indicates that platelets release a substance(s) which enhances basophil response to IgE dependent activation, Knauer et al., *N Engl J Med* 306: 1407 (1981), Knauer et al., *Int Arch Allergy Appl Immunol* 74:29 (1984). Further data suggest that a substance released by platelets could also directly cause basophil degranulation, potentially by an IgE dependent mechanism, Orchard et al., *Thromb Haemostas* 54:232 (1986); Orchard et al., *J Immunol* 136:22 (1986). Additional research has indicated that platelets are activated during exercise induced asthma, and that platelet activation is prevented by premedication with inhaled cromolyn, Johnson et al., *Thorax* 41: 290 (1986). A role for platelets with regard to allergic inflammation was further suggested by the finding that they can bind IgE via a low affinity receptor, thereby permitting direct activation by exposure to allergen, Cines et al., *J Immunol* 136: 3433–3440 (1986), and also that platelet depletion in rabbits reduces late phase asthmatic response, including hyperresponsiveness and eosinophilic inflammation. Coyle et al., *Am Rev Respir Dis*, 142:507–593 (1990).

It was recently shown that a protein produced by platelets, termed Platelet-Derived Histamine Releasing Factor (PD-HRF), causes basophil degranulation only in allergic subjects. See Fisher et al., *J Allergy Clin Inmmunol* 79:196 (1987). In-vivo skin testing in humans with PD-HRF obtained from platelet supernatant demonstrated that allergic asthmatics developed reactions, but normal subjects or subjects with allergic rhinitis without asthma did not. Weiss et al. *J Allergy Clin. Immunol* 81: 224 (1988). In a study designed to further define the role of PD-HRF in asthma, in-vivo bronchial challenges of allergic asthmatic rabbits using PD-HRF-containing supernatants caused early and late airway obstruction and increased hyperresponsiveness in the subjects. Fisher et al., *Aspen Allergy Conference* (1990); Metzger et al., *J. Allergy Clin Immunol* 85(1) (1990).

SUMMARY OF THE INVENTION

The present invention provides a method of treating asthma in a subject in need of such treatment. The method comprises administering an active agent to the subject by contacting the active agent to the respiratory epithelium of the subject. The active agent is Asthma Reversal Factor, an active fragment of asthma reversal factor, or an analog thereof. The active agent is administered to the subject in an effective asthma-combatting amount. The active agent is preferably contacted to the subject's respiratory epithelium by causing the subject to inhale respirable particles (i.e., liquid particles or solid particles) which include the active agent.

A second aspect of the present invention is a composition comprised of an active agent selected from the group consisting of Asthma Reversal Factor (ARF), active fragments of ARF, and analogs thereof in a pharmaceutically acceptable carrier.

A third aspect of the present invention is the use of an active agent as given above for the preparation of a medicament for treating asthma.

A fourth aspect of the invention is isolated Asthma Reversal Factor, characterized by having a molecular weight of between about 8 and 12 kDa as measured by SDS-polyacrylamide gel electrophoresis and by HPLC, binding weakly to heparin, and capable of inhibiting histamine release from basophils of asthma patients.

A fifth aspect of the invention is asthma reversal factor produced by the process of:
(a) rinsing blood platelets with an aqueous solution to produce washed blood platelets;
(b) combining the washed blood platelets with a salt solution to produce a suspension thereof;
(c) separating the blood platelets from the suspension;
(d) contacting the suspension to heparin, wherein the heparin is immobilized on a solid support, so that the Asthma Reversal Factor is bound to the solid support;
(e) separating the suspension from the solid support;
(f) washing the solid support with a 2M NaCl aqueous salt solution to release the Asthma Reversal Factor from the solid support into the 2M aqueous salt solution.

DETAILED DESCRIPTION OF THE INVENTION

Figure 1:
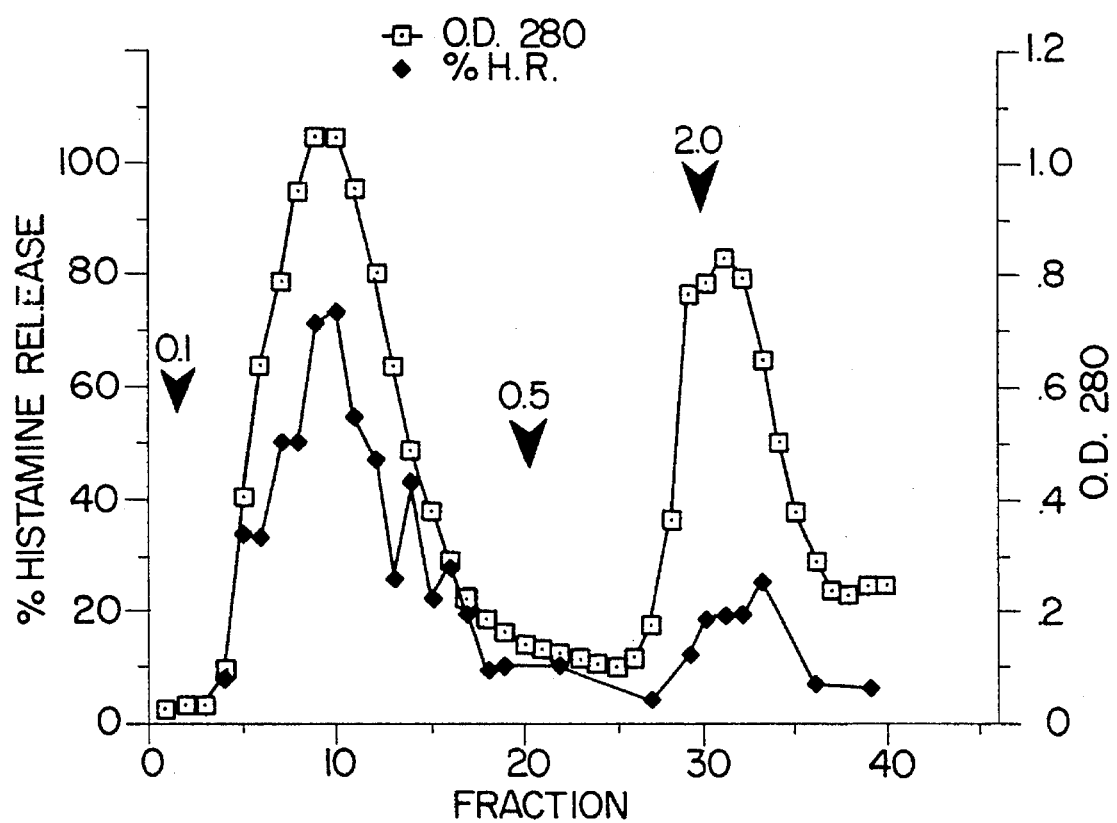
FIG. 1 is a graph plotting the histamine release caused by platelet supernatant fractions. PD-HRF activity was predominantly present in the non-adherent protein (0.1M) peak, while ARF activity was present in material eluted with 2.0M NaCl.

The present invention is useful for combatting all types of asthma and allergic rhinitis. For the treatment of allergic rhinitis the active agent need only reach the subject's nasal epithelia. For this purpose an aqueous solution carrying the active agent may be topically applied to the nasal epithelium in the form of particles, droplets, or solutions.

The present invention can also be used to treat fibromyalgia, a syndrome of tiredness and generalized aching also known as "tension-fatigue syndrome" often attributed to seasonal allergen exposure. See Cleveland et al., *Allergy Proceedings* (in press 1992). Symptoms include widespread pain for at least three months in combination with tenderness in at least 11 of 18 specific sites. Symptoms are often exacerbated by exercise, lack of sleep, stress, chronic headache, irritable bowel syndrome, and numbness. When used for treating fibromyalgia, the active agent is preferably administered by contacting it the subject's respiratory epithelia. However, other routes of administration may also be employed when treating this condition, including oral administration and parenteral administration (i.e., subcutaneous injection, intravenous injection, intramuscular injection).

The term "Asthma Reversal Factor" (ARF) as used herein means the polypeptide produced by and found in the supernatant of mammalian thrombocytes. ARF is produced by both thrombocytes stimulated with Platelet-Derived Histamine Releasing Factor (PD-HRF) or some other agent, such as thrombin, and by unstimulated thrombocytes. The protein has a molecular weight of between about 8 and 12 kDa as measured by SDS polyacrylamide gel electrophoresis, is weakly bound by heparin, and shares considerable homology with Interleukin-8. The ARF may be of any species of origin, such as bovine, ovine, porcine, rabbit, and human, but is preferably of mammalian origin. Particularly preferred for practicing the present invention is human thrombocyte ARF. The ARF may be produced by any suitable means, including by recombinant means in cells which do not typically produce ARF, and by culture of cells which ordinarily produce ARF. A preferred cell culture for producing ARF is the HEL cell line.

Isolated ARF of the present invention may be produced in the manner described below, or variations thereof which will be apparent to those skilled in the art. Isolated ARF is further purified, and/or purified sufficiently for amino acid sequencing, in accordance with known techniques, such as with high performance liquid chromatography (HPLC), affinity chromatography (e.g., with antibodies to the protein, or with a heparin, lectin, or with propyl sulfonic acid functional group affinity column), comprehensive two-dimensional high performance liquid chromatography coupling ion exchange chromatography and size exclusion chromatography (see M. Bushey and J. Jorgenson, *Analytical Chemistry* 62:161–167 (1990)), two-dimensional HPLC/Capillary zone electrophoresis (see, e.g., M. Bushey and J. Jorgenson, *Analytical Chemistry* 62:978–984 (1990)) and variations thereof (i.e., where other liquid chromatography columns such as reverse phase chromatography columns, ion exchange chromatography columns, adsorption chromatography columns, and affinity chromatography columns are used; or where other capillary electrophoresis apparatus such as capillary gel electrophoresis, capillary isotachophoresis, micellar electrokinetic capillary chromatography, and capillary isoelectric focusing are used), other multidimensional separation systems (see J. Giddings, *J. High Resolut. Chromatogr. Chromatogr. Commun.* 10:319–323 (1987)), SDS-polyacrylamide gel electrophoresis, two-dimensional polyacrylamide gel electrophoresis such as disclosed in R. Broglie et al., *Plant Mol. Biol.* 3:431–444 (1984), etc.

Active fragments of ARF are peptides derived from ARF which have N-terminal, C-terminal, or both N-terminal and C-terminal amino acid residues deleted, but retain the biological activity of ARF as described herein. Active fragments may be glycosylated or unglycosylated, with glycosylated fragments generally being preferred. Active fragments may exist as monomers or multimers (e.g., dimers). Such active fragments may be prepared by enzymatic digestion of ARF, by direct synthesis, or by genetic engineering procedures. The active fragments suitable for use in the present invention may or may not share homology with Interleukin-8 active fragments. Where homology is shared, the active fragments may be 60, 70, 80 or even 90 percent homologous or more; where homology is not shared, the active fragments may be no more than 50, 40, 30, or even 20 percent homologous. Active fragments may contain 50, 60, 70 or 80 amino acids or more, or may contain as few as 40, 30, 20, or even 10 amino acids.

Derivatives of ARF and active fragments thereof are, in general, analogs thereof. An "analog" is a chemical compound similar in structure to another which has either a similar or opposite physiological action. Thus, analogs of ARF and analogs of active fragments of ARF are in general peptides. Such analogs may be prepared by altering or deleting amino acids. One or more amino acids of a synthetic peptide sequence may be replaced by one or more other amino acids which does not affect the antigenicity of that sequence. Such changes can be guided by known similarities between amino acids in physical features such as charge density, hydrophobicity/hydrophilicity, size and configuration. For example, Thr may be replaced by Ser and vice versa, Asp may be replaced by Glu and vice versa, and Leu may be replaced by Ile and vice versa. Further, those skilled in this art will appreciate that minor changes may be made to the naturally occuring amino acids to produce derivatives thereof which retain activity. Analogs may be agonists (compounds having similar biological activity to ARF), or may be antagonists (compounds having the opposite bioloigcal activity to ARF), with agonists being preferred.

The amount of active agent administered to the subject will vary depending upon the age, weight, condition of the subject, and the particular disorder or disorders being treated, but is generally from 0.1 nanograms to 10 micrograms, and is typically an amount ranging from 1 nanogram to 1 microgram. Medicaments are formulated as discussed below to deliver this quantity of the active agent to the lungs of a patient by inhalation, or to the nasal respiratory epithelium as a topically applied liquid medicament.

Aerosol particles (solid or liquid) for practicing the present invention are preferably particles of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable.

Compositions containing the active agent of the present invention may be prepared in either solid or liquid form.

To prepare the pharmaceutical compositions of this invention, one or more compounds of salt thereof of the invention as the active ingredient, is intimately admixed with a pharmaceutical carrier according to conventional pharmaceutical compounding techniques, which carrier may take a wide variety of forms depending on the form of preparation desired for administration, e.g. oral, inhalation or parenteral. In preparing the compositions in oral dosage form, any of the usual pharmaceutical media may be employed. Thus, for liquid oral preparation, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservatives, may be included. Injectable suspensions may also be prepared, in which case appropriate liquid carriers, suspending agents and the like may be employed.

For administration by inhalation, compositions containing respirable dry particles of micronized active agent may be prepared by grinding dry active agent with a mortar and pestle, and then passing the micronized composition through a 400 mesh screen to break up or separate out large agglomerates. Liquid compositions comprise the active agent dispersed in an aqueous carrier, such as sterile pyrogen free saline solution or sterile pyrogen free water. If desired, the composition may be mixed with a propellant to assist in spraying the composition and forming an aerosol thereof. The solid particulate form of the active agent may optionally contain a dispersant which serves to facilitate the formation of an aerosol. A suitable dispersant is lactose, which may be blended with the active agent in any suitable ratio (e.g., a 1 to 1 ratio by weight). The medicament compositions may be provided in unit dosage form, such as in the form of sterile ampoules or pressurized containers.

Active agents of the present invention may be administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of a carboxylic acid group.

Liquid aerosols of respirable particles may be administered by any suitable means, such as by nebulizing a liquid composition containing the active agent (e.g., with a jet nebulizer or an ultrasonic nebulizer), and causing the patient to inhale the nebulized composition. Alternatively, patients maintained on a ventilating apparatus can be administered an aerosol of respirable particles by nebulizing the liquid composition and introducing the aerosol into the inspiratory gas stream of the ventilating apparatus, as described in U.S. Pat. No. 4,832,012 to Raabe and Lee (the disclosure of which is to be incorporated herein by reference).

Any solid particulate medicament aerosol generator may be used to practice the present invention, with specific examples being given below. Aerosol generators for administering solid particulate medicaments to a human subject produce particles which are respirable, as explained above, and generate a volume of aerosol containing a predetermined metered dose of a medicament at a rate suitable for human administration. One illustrative type of aerosol generator comprises a chamber having a rotor mounted therein, which rotor carries a gelatin capsule containing a metered dose of dry particle medicament. In use the capsule is pierced, a patient inhales through the chamber, and the rotor is caused to spin at a speed sufficient to dispense the medicament to thereby form an aerosol of dry particles. A second type of illustrative aerosol generator is a metered dose inhaler comprising a pressurized canister containing dry particle medicament in an aerosol propellant (e.g., a chlorofluorocarbon propellant, a hydrofluorocarbon propellant, etc.) with a valve configured to deliver a metered dose of the active agent to a patient. The propellant is discharged through a metering valve configured to dispense a metered dose of the dry particle medicament into the atmosphere. The propellant evaporates, leaving an aerosol of dry particle medicament.

The present invention is explained in greater detail in the following non-limiting examples. In these examples, "M" means molar concentration, "mM" means millimoles, "g" means grams, "mg" means milligrams, "µg" means micrograms, "ng" means nanograms, "kg" means kilograms, "ml" means milliliters, "µl" means microliters, "cm" means centimeters, "mm" means millimeters, "nm" means nanometers, and "° C." means degrees Centigrade.

EXAMPLE 1

Administration of Crude PD-HRF Extract to Asthmatic Rabbits

In a study designed to further define the role of PD-HRF in asthma, in-vivo bronchial challenges of allergic asthmatic rabbits using PD-HRF-containing supernatants caused early and late airway obstruction and increased hyperresponsiveness in the subjects. However, when these rabbits were re-tested 1 month after challenge, their hyperreactivity had disappeared. This indicates that a substance was present in the PD-HRF containing supernatant which had the ability to reverse asthma; this substance was termed asthma reversal factor (ARF).

EXAMPLE 2

Inhibition of Basophil Histamine Release

Basophil histamine release assays have been well described and are carried out in a similar manner to that of Orchard et al. *J. Immunol.* 136:22 (1986). Human blood was drawn in a sufficient amount that approximately 20,000 basophils were available for each reaction tube. When performing PD-HRF inhibition assays, blood was obtained from allergic subjects who are known to have basophil degranulation in response to PD-HRF. Normal humans or those with mild allergic rhinitis but no asthma are used as basophil donors for hyperosmolar inhibition assays. After the blood was drawn, 20 ml aliquots are placed in tubes containing dextran (6.25 ml, 1% final concentration) and ethylenediaminetetraacetic acid (EDTA) (2.5 ml, 10 mM final concentration). The blood was allowed to sediment by gravity for 90 minutes at room temperature, and the upper layer containing platelet rich plasma (PRP) and mixed leukocytes was then centrifuged at 150×g for 9 minutes at 21° C. The resultant supernatant consisting of PRP was saved for human ARF isolation. The mixed leukocyte pellet containing basophils was washed twice in a buffer containing 25 mM (piperazine-N,N'-Bis[2-ethanesulfonic acid]:1, 4-piperazinediethanesulfonic acid (PIPES), 110 mM NaCl, 5 mM KCl, 0.003% human serum albumin (HSA) and 0.1% D-glucose (pH 7.40) (PAG). The cells were then resuspended in $PC_2G$ (identical to PAG but with 2 mM $CaCl_2$ substituted for albumin) and 50 μl aliquots are placed in reaction tubes.

Purified or partially purified ARF obtained from chromatography was dialyzed against $PC_2G$ using a 3,500 molecular weight cutoff membrane in advance. For in-vitro assay, ARF which exhibited an optical density of between 0.001 to 0.1 units (typically 0.01) at 280 nanometers was used for in-vitro assay. 10 μl aliquots of such ARF was added to tubes containing leukocytes and allowed to incubate for 15 minutes at 37° C. After 15 minutes, additional stimuli and $PC_2G$ buffer were added to each tube to provide a final volume of 100 μl.

One set of duplicate tubes contained only cells plus buffer to determine spontaneous release of histamine. Stimuli added to tubes included: a) perchloric acid (2% final concentration) to determine total histamine content; b) goat anti-human IgE (0.1 μg/ml) as a positive control; c) mannitol in $PC_2G$ yielding a final osmolarity of 735 mOsm; and d) PD-HRF. A matching set of tubes with cells, stimuli and buffer but no ARF was also prepared to assess the release each stimulus causes without the influence of ARF. After a 45 minute incubation at 37° C., the reaction was stopped by the addition of 900 μl of cold PAG, and the suspension was centrifuged at room temperature at 1,000×g for 2.5 minutes. The resultant supernatant was then assayed for histamine content using an automated fluorometric assay. See Siraganian, *J. Immnol. Meth.* 7:283 (1975).

The percent histamine released was calculated by subtracting the spontaneous release from that of the unknowns and dividing by the total content. The percent inhibition of histamine release caused by ARF-containing fractions is calculated by subtracting percent release caused by stimulus plus ARF from percent release from stimulus alone, and then dividing by percent release caused by stimulus alone. These values were used to quickly determine which fractions of column eluant were active and therefore likely to contain ARF.

EXAMPLE 3

ARF Preparation—Scheme 1

ARF is obtained from platelets found in the peripheral blood. A supernatant was formed in a manner similar to that described in Orchard et al., *J. Immunol.* 136: 22 (1986). Human blood was drawn and placed in an anticoagulant mixture of 1% dextran and 10 mMEDTA. Red blood cells were removed by sedimentation at room temperature for 90 minutes, then the upper layer was centrifuged at 150×g for 9 minutes to remove leukocytes. The remaining platelet-rich plasma was centrifuged for 20 minutes at 1,000×g to pelletize the platelets, and the platelets were washed twice in a phosphate buffer (112 mM NaCl, 4 mM $K_2HPO_4$, 6 mM $Na_2HPO_4.7H_2O$, 25 mM $NaH_2PO_2.H_2O$, and 0.1% D-glucose) containing 3.5 mM EDTA. The platelet preparation was 99.7% pure after washing, with 0.2% contamination in the form of red cells and 0.1% from mixed leukocytes. Platelets were resuspended in a 25 mM PIPES buffer containing 1 mM calcium, 110 mM NaCl, 5 mM KCL and 0.1% D-glucose. The suspended cells were counted to determine concentration; then the concentration was adjusted to $6 \times 10^8$ platelets/ml (about 2–3 times the concentration in blood). The platelets were then gently stirred in a glass flask for 15 minutes at 37° C. The supernatants were collected by centrifuging the mixture at 2,300×g for 20 minutes, then were dialyzed against 1/10th buffer using a 3,500 molecular weight cutoff membrane for 24 hours to remove low molecular weight contaminants, lyophilized, and resuspended to concentrate the solution thirty-fold.

Next, ARF was isolated from the supernatants. Preliminary assay work as described in Example 2 demonstrated that the portion of platelet supernatant that causes histamine release (PD-HRF) did not bind heparin (FIG. 1), so the supernatants were dialyzed against 0.1M NaCl, 0.01M tris(hydroxymethyl)aminoethane (tris) for 24 hours, then eluted in a heparin-agarose column (Sigma, St. Louis, Mo.) with 0.1M NaCl, 0.01M tris. The column was then washed with 2.0M NaCl, 0.2M tris. The 2M eluate pool was dialyzed against the 1/10 PIPES buffer for 24 hours, lyophilized, resuspended and dialyzed against 0.9% saline-containing 2 mM $CaCl_2$ to increase concentration tenfold. This material, which contained ARF, was then used for the rabbit inhalation described in Example 12. Autologous blood and disposable columns have been used for human studies.

EXAMPLE 4

ARF Preparation—Scheme 2

An alternative strategy for the isolation of ARF is one similar in principle to that used in the isolation of another trace protein, plasminogen activator inhibitor, from porcine platelets. Blood is collected into plastic buckets (approximately 10 liters each) containing one tenth volume of a solution comprising 0.4% citric acid, 1.3% trisodium citrate, 1.5% dextrose and 25 mM EDTA. This anticoagulant is stirred into the blood and the blood transferred to capped plastic containers for transport to the laboratory. Platelets are then isolated from the plasma by centrifugation at greater than 100 g for 15 minutes. The platelet pellet is washed three times in 5 liters of a solution comprising 0.15M NaCl, 10 mM tris-HCl and 2.5 mM EDTA (pH 7.5), then washed one final time in 2 liters of the same solution. The platelets are resuspended in 200 ml of the wash buffer and stored frozen at −80° C.

For ARF isolation, platelets are thawed, phenylmethyl-sulfonyl fluoride (PMSF) is added to a concentration of $2 \times 10^{-4}$M, and the broken cells are centrifuged at 10,000 RPM for 10 min at 4° C. The platelet lysate supernatant is removed; the pellet is resuspended in a solution comprising 50 mM NaCl, 25 mM Tris HCl, 1 mM EDTA, 1 mM benzamidine and 0.01% CHAPS (pH 7.6) (column buffer), refrozen, thawed and recentrifuged. The supernatants are combined, 2M citric acid is added to acidify the solution to pH 2.0, and after 30 minutes the pH is adjusted to 7.6 with 2M Tris. The pooled lysate is then dialyzed against column buffer overnight. The dialyzed sample is centrifuged at 10,000 RPM to remove precipitated protein and eluted in a 0.9×30 cm column of heparin-sepharose Cl-7B (Pharmacia LKB Biotechnology, Inc., Piscataway N.J.) previously equilibrated with column buffer. Following sample introduction, the column is washed with column buffer until the light absorbance at 289 nm returns to its baseline value. Proteins are then eluted with a gradient of NaCl solution ranging in concentration from 0.1M to 2.0M in the column buffer.

The material shown to inhibit histamine release elutes from the column from 0.2–0.6M NaCl. The active fraction elutes prior to elution of the protein peak corresponding to β-thromboglobulin and after the major protein peak eluted from the column at lower salt concentration. Fractions containing the inhibitory activity are pooled, dialyzed against 4 liters 0.05M NaCl, 0.01 M Tris HCl to lower the salt concentration, and concentrated by lyophilization (not to dryness). This sample (5–6 ml) is applied to a Sephacryl S-200 column and eluted with 1M NaCl, 0.01M Tris, pH 7.4. The results from assay of this column indicate that the fraction exhibiting the major inhibitory activity has little, if any, absorbance at 280 nm, but does absorb at 214 nm, and elutes from the column in latter fractions, suggesting an apparent molecular weight less than 18 kDA.

EXAMPLE 5

Purification of ARF

Because the material produced by the procedure of Example 3 is present in low concentration and appears to be of fairly low molecular weight, further purification can rely on the use of high performance liquid chromatography (HPLC). Initially the active fraction would be concentrated, applied to Vydac C4 column, and eluted with an increasing gradient of acetonitrile in 0.1% aqueous trifluoroacetic acid. The utility of this step may depend on recovery of biologically active material from this acidic eluant.

Possible alternative chromatographic steps at this point include hydrophobic interaction, lectin affinity, or rechromatography on a column with propyl sulfonic acid functional groups. It is anticipated that these methods will yield material suitable for amino terminal sequencing of the intact protein. This would provide information to determine the identity of ARF and permit cloning of the cDNA and gene for further structural characterization.

EXAMPLE 6

Molecular weight Determination of ARF

Figure 2:
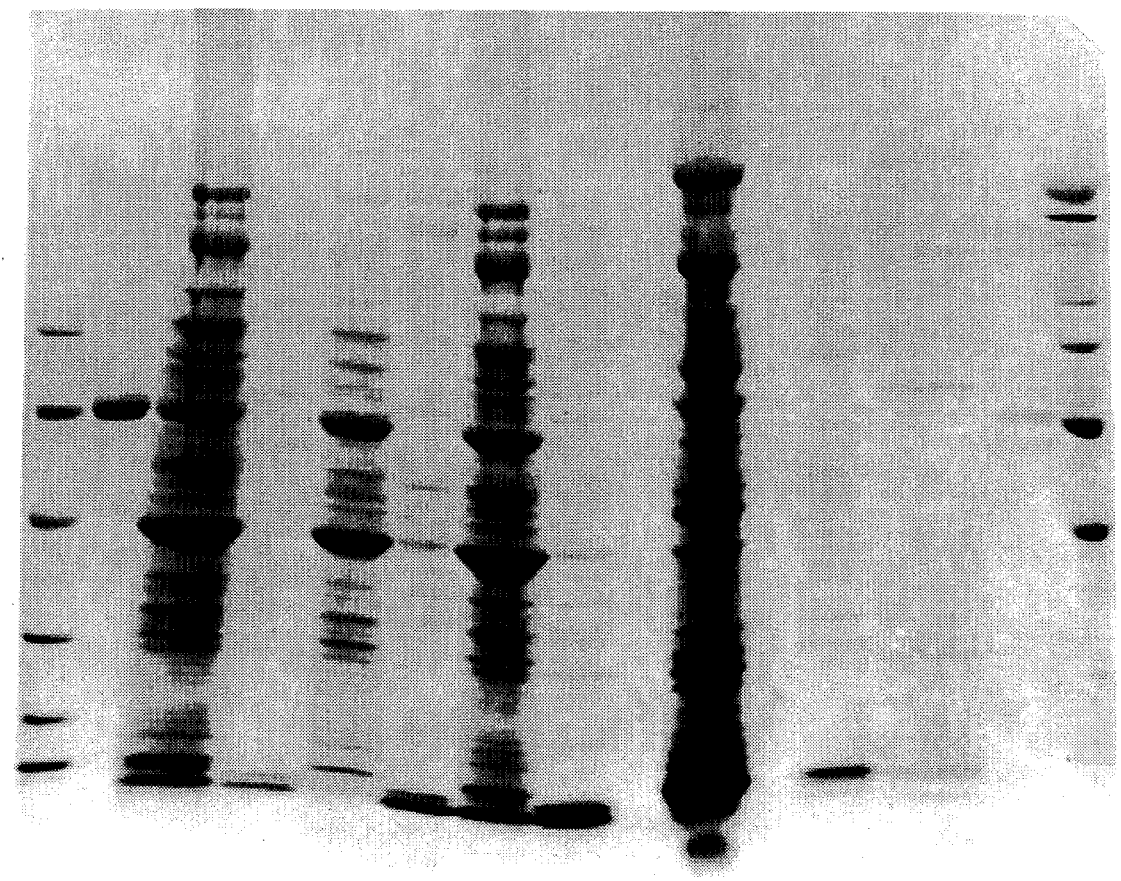
FIG. 2 is a SDS-PAGE gel of material eluted from disposable heparin columns. Lanes 4, 6, and 8 are ARF fractions of three different human patients; Lanes 3, 5, and 7 are PD-HRF fractions for the same patients. Lane 9 is a porcine platelet supernatant. Lanes 10 and 11 are porcine ARF fractions. Lanes 1 and 13 are molecular weight standards, and Lanes 2 and 12 are albumin.
Figure 3A:
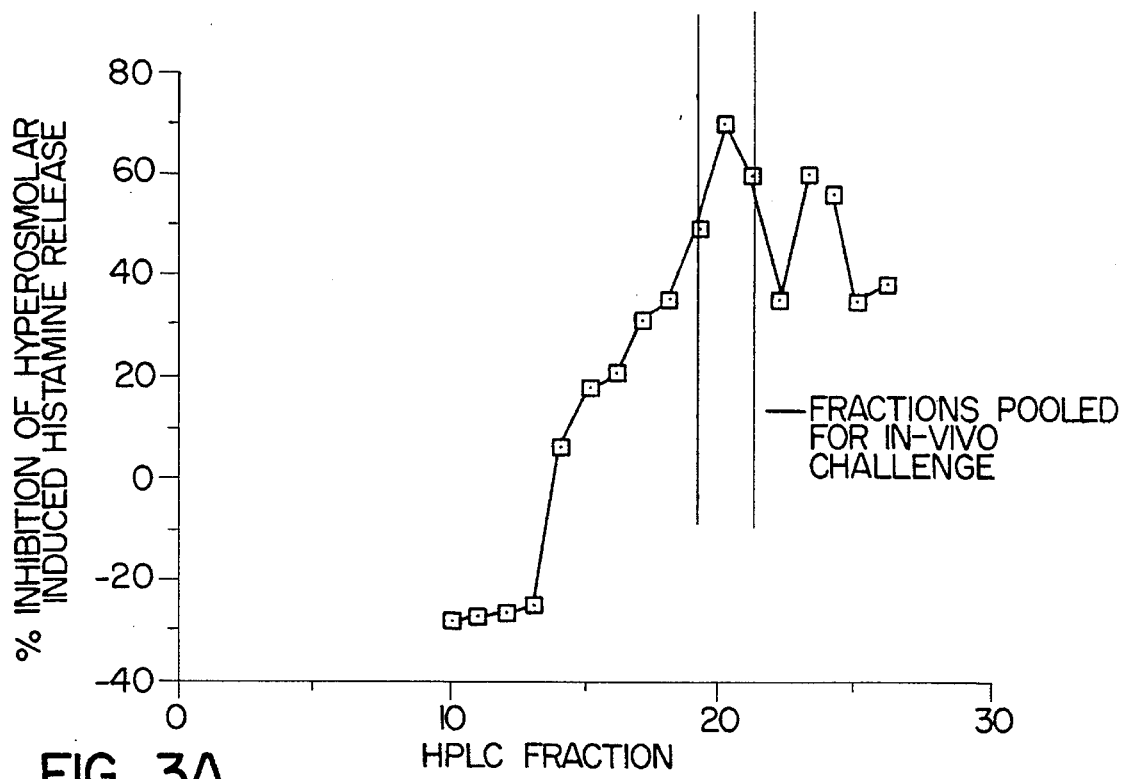
FIG. 3A is a plot of the inhibition of histamine release as a function of HPLC fraction; the fractions used for in vivo challenge are shown as fractions 19–21.
Figure 3B:
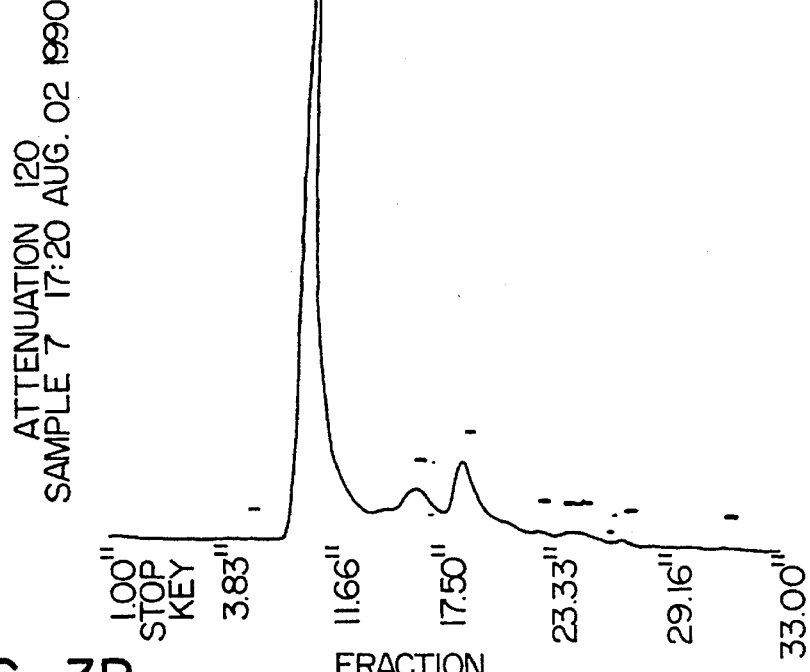
FIG. 3B shows the protein peaks of the HPLC fractions of FIG. 3A. Fractions 19–21 correspond to the third protein peak of FIG. 3B; the molecular weight of the proteins comprising this peak was calculated to be approximately 10 kDa.

The molecular weight of ARF was assessed by both SDS-polyacrylamide gel electrophoresis (SDS-PAGE) using silver staining and HPLC gel filtration. ARF activity was found to be associated with a low molecular weight (8–10 Kd) protein which weakly binds heparin (0.2M–0.5M NaCl). ARF obtained from each of three human subjects who improved clinically after ARF inhalation (see Example 14) showed a low molecular weight double band pattern present in SDS-PAGE gel (FIG. 2). Heparin-adherent material with ARF activity was further subjected to HPLC gel filtration to determine molecular weight. FIGS. 3A and 3B show that material found to reverse hyperreactivity in 2 rabbits (see Example 12) had a molecular weight of approximately 10 kDa by a Waters SW 300 HPLC gel filtration column.

EXAMPLE 7

Immunological Characterization of ARF

Figure 4:
FIG. 4 is a dot blot of three ARF fractions of different concentrations, human recombinant IL-8 at 100 ng/ml and at 2 µg/ml, and rabbit anti-IL-8. Dots were incubated against specific rabbit-anti-IL-8 and then were detected by goat anti-rabbit linked to peroxidase. The visible dots are the ARF fractions and the higher concentration of human IL-8.

Further studies designed to characterize the immunologic behavior of ARF were performed. Because ARF has similarities to IL-8 based upon its molecular weight and binding characteristics to heparin, a dot blot study was perform to compare its immunological properties to those of IL-8. Samples (30 μl) of 3 different concentrations of ARF were applied to a nitrocellulose membrane. As positive controls, 30 μl samples of 100 ng/ml and 2 μg/ml human recombinant endothelial IL-8 (Genzyme, Boston, Mass.) and of a specific polyclonal rabbit-anti-human IL-8 (Endogen, Boston, Mass.) were also applied to the membrane. The membrane was washed, the binding sites were blocked with HSA, and a peroxidase-linked goat anti-rabbit antibody was used for detection using an Enzygraphic Web (Kodak, Rochester, N.Y.). As seen in FIG. 4, the goat-anti rabbit antibody was found to bind rabbit antibody to the 3 samples of ARF as well as the control rabbit antibody spot and the 2 μg/ml human IL-8 spot. Detectable binding was not seen for the lower, 100 ng/ml concentration of human IL-8, nor was non-specific binding seen to the HSA on the membrane.

In a separate procedure designed to cross-check binding selectivity, partially purified ARF was injected in a rabbit which received 3 booster immunizations (one every 2–3 weeks) to raise antibody. Serum from this rabbit was obtained and used for dot blotting. The rabbit serum gave positive dots against both ARF and recombinant human IL-8. These anti-ARF antibodies also detected a band on Western blotting which corresponded to IL-8.

These results indicate that ARF and IL-8 have immunologic cross reactivity, perhaps through amino acid homology.

EXAMPLE 8

Characterization of Heparin-Binding Properties of ARF

Figure 5:
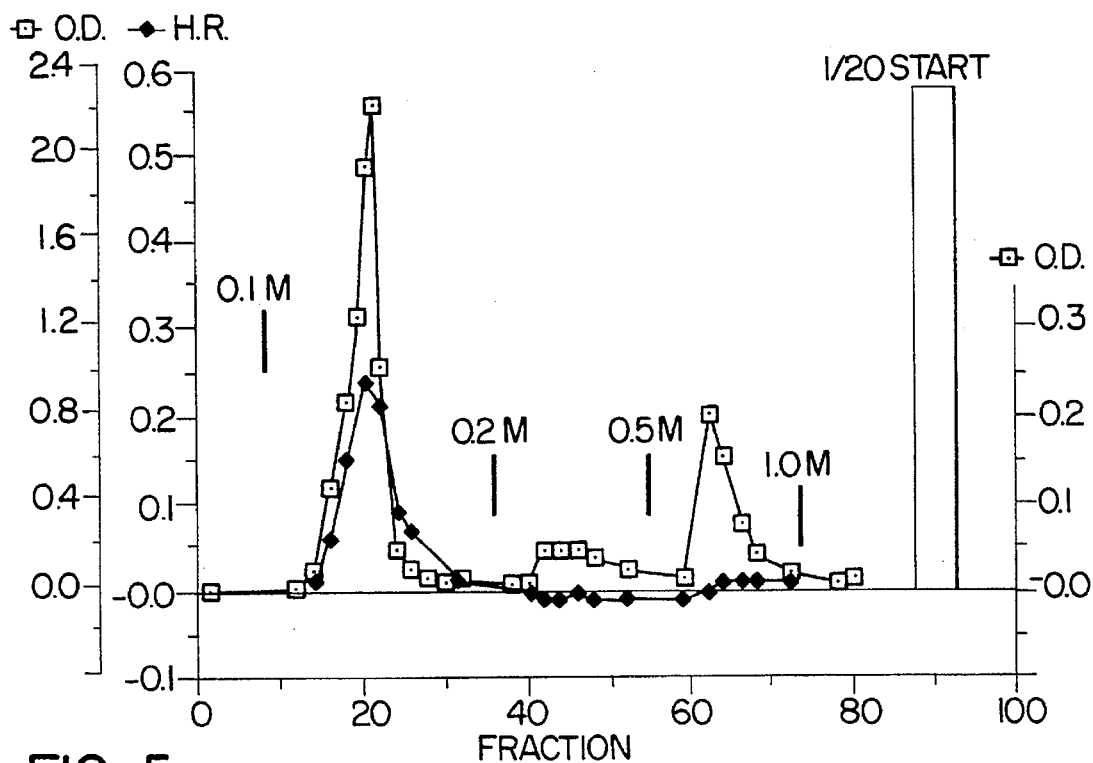
FIG. 5 is a plot of histamine release and protein concentration of fractions of human platelet supernatant eluted with an NaCl gradient. Only the middle peak (0.2–0.5M NaCl) caused reversal of hyperresponsiveness in rabbit subjects; the other peaks exacerbated asthma symptoms.
Figure 6:
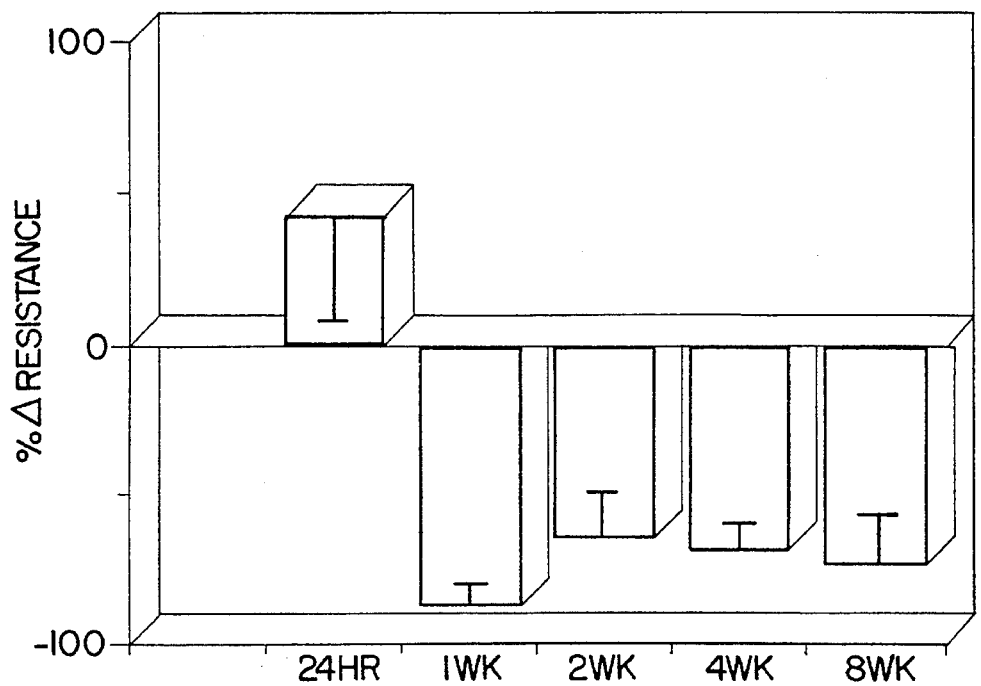
FIG. 6 is a plot of airway resistance as a function of time which shows that ARF inhalation increases resistance for the first 24 hours, but significantly reduces resistance in rabbits for at least 2 months.
Figure 7:
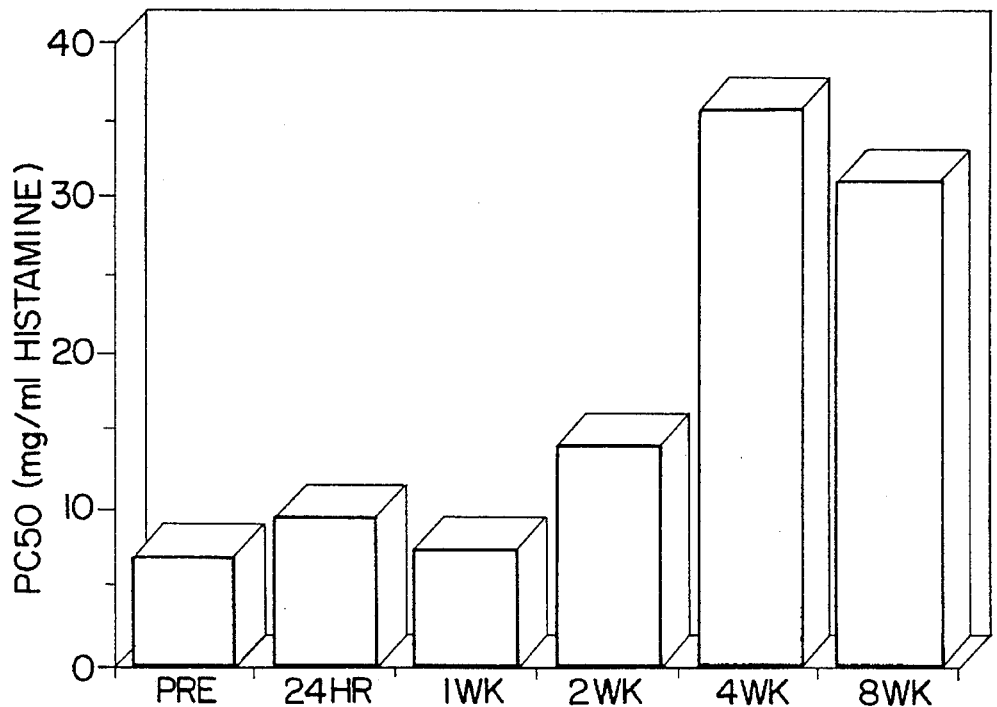
FIG. 7 is a plot of $PC_{50}$ as a function of time following inhalation which illustrates that a single ARF treatment in allergic rabbits results in airway hyperresponsiveness being significantly lower than that of the baseline value at weeks 2–8.

To further characterize the heparin binding properties of ARF, elution from heparin-agarose using a salt gradient was carried out (FIG. 5). Three major peaks of protein were eluted, one each at 0.1M, 0.2–0.5M, and 1M NaCl. These fractions were assessed for their ability to inhibit in-vitro hyperosmolar induced histamine release (Example 2); the second (0.2M–0.5M) peak exhibited desirable in-vitro activity. In addition, inhalation of the material of the latter peak also caused obstruction and hyperreactivity in subsequent animal studies, but the 0.2–0.5M peak reversed hyperreactivity (see Example 13). The second peak was further subjected to SDS-PAGE and HPLC gel filtration and determined to have a molecular weight of 8–12 kDa (Example 6). This 8–12 kDa peak from HPLC analysis was used to challenge 2 asthmatic rabbits and was found to reverse asthma, thus confirming that the material which weakly bound heparin contained ARF.

EXAMPLE 9

PD-HRF preparation

Human PD-HRF can be prepared in a manner similar to that described above by Orchard et al. After a crude platelet supernatant containing ARF and PD-HRF activity was obtained and passed over a heparin affinity column, the non-adherent protein eluted from the column with 0.1M NaCL was collected. This fraction was dialyzed against 1:10 $PC_2G$, concentrated 30 fold by lyophilization, redialyzed into $PC_2G$, and divided into 10 μl aliquots for use as a stimulus as described in Example 2 above.

EXAMPLE 10

Rabbit Preparation

Pasteurella-free New Zealand white rabbits were used for animal studies. Rabbit does were initially obtained commercially, and then litters of rabbits were raised in the animal care facility of East Carolina University School of Medicine. Neonatal rabbits were immunized intraperitoneally within 24 hours of birth with 0.5 ml of 1 mg/ml ragweed (Greer, Lenoir, N.C.), or 612 AU/ml of Dermatophagoides farinae, mixed with 10% kaolin in saline. These immunizations were repeated weekly for the first month, and then bi-weekly for the next 2–3 months.

EXAMPLE 11

Bronchial Measurements of Rabbit Subjects

Adult rabbits (2.5–3.5 kg) were anaesthetized and relaxed with a mixture of ketamine hydrochloride (35 mg/kg) (Vince Products, Syracuse, N.Y.) and acepromazine maleate (1.5 mg/kg) (Aveco Co., Inc., Fort Dodge, Iowa) to permit intubation (Coyle 1990). Each rabbit was laid supine and intubated with a 4.0 mm endotracheal tube (Mallinckrodt, Inc., Glens Falls, N.Y.), which was attached to a heated Fleisch pneumotachograph (size 00) (DOM Medical Inc., Richmond, Va.); flow was measured with a Validyne pressure transducer (Validyne Engineering Corp., Northridge, Calif.—Model DP-45-16-1927) driven by a Gould carrier amplifier (Model 11-4113, Gould Electronics, Cleveland, Ohio). Pleural pressure was estimated by placing an esophageal balloon in the lower third of the esophagus to obtain maximal pressure changes. Transthoracic pressure was measured by a side-hole connected to the distal end of the tracheal tube. Transpulmonary pressure, the difference between pleural pressure and thoracic pressure, was measured by a Validyne differential pressure transducer. These were attached to a Buxco automated pulmonary mechanics analyzer (Model 6, Buxco Electronics Inc., Sharon, Conn.), and flow was integrated to elicit a continuous tidal volume. Measurements of lung resistance ($R_L$) and dynamic compliance (Cdyn) were calculated at isovolumetric points and zero flow points, respectively, as described in detail previously (Giles, Finkel et al. 1971). Bronchial hyperresponsiveness was determined by calculating the dose of histamine (mg/ml) required to reduce the Cdyn by 50% from baseline ($PC_{50}$).

EXAMPLE 12

Administration of ARF to Rabbits

Histamine (0.139–80 mg/ml), was delivered with a DeVilbiss nebulizer (DeVilbiss Co., Somerset, Pa.) for 2 minutes at 2 minute intervals for each administration; airway resistance, dynamic compliance, and $PC_{50}$ measurements were taken to establish baseline values. The following day, ARF was administered in a 0.9% saline solution with 2 mM $CaCl_2$ with a handheld DeVilbiss nebulizer. First, 1 ml of a 1/1000 mixture of ARF/saline was administered over a two minute period. After the subject was observed for 5 minutes, the procedure was repeated with 1 ml of a 1/100 ARF/saline mixture. After a second 3–5 minute observation period, a final 1 ml 1/10 dosage was administered. The subjects were monitored for airway resistance, dynamic compliance at hours 1–6. $PC_{50}$, $R_L$, and dynamic compliance were measured at 24 hours and again after 1, 2, 4 and 8 weeks.

EXAMPLE 13

Results of Rabbit Challenges with PD-HRF and ARF

Five rabbits challenged with PD-HRF fractions either rapidly died from respiratory distress or developed prolonged obstruction with increased hyperresponsiveness (lasting weeks to months). Rabbits challenged with material that had adhered to heparin (thus depleted of PD-HRF) which was then eluted with 2M NaCl developed a mild degree of late phase obstruction, but were later found to have a long-lived, statistically significant improvement in airway resistance (FIG. 6). These rabbits also experienced a significant reduction in airway hyperreactivity (FIG. 7). Thus, not only was ARF challenge well tolerated in the rabbits, but the beneficial effects of reduced hyperresponsiveness and obstruction were long lived after a single administration.

The mechanism of this response is not currently understood. Our studies indicate that in-vitro basophil response to hyperosmolar stimuli (mannitol) is blocked by ARF, and this assay has been used to test fractions for activity during purification. Hyperosmolar secretions are thought to trigger mast cell and basophil degranulation in humans and be the cause of exercise induced asthma (Ingenito et al., "Dissociation of temperature-gradient and evaporative heat loss during cold gas hyperventilation in cold-induced asthma." *Am Rev Resp Dis* 138: 540 (1988). Routinely, fractions with in-vivo activity will inhibit histamine release from basophils by 20–50%. In addition, ARF may block eosinophil migration into sites of inflammation. When 2 allergic rabbits which had received ARF were challenged with appropriate allergen 1 month following ARF induced asthma reversal, the allergen challenge failed to induce hyperreactivity or bronchial eosinophilia despite the ability to induce these changes prior to ARF therapy.

EXAMPLE 14

Administration of ARF in Humans 100 ml of blood was drawn from a peripheral vein and processed as described above to produce autologous ARF. Prior to inhalation, the ARF was diluted 10 fold in 0.9% saline containing 2 mM $CaCl_2$. This material was then passed through a sterile 0.22 µm filter, collected, and diluted in serial 10 fold dilutions. Material obtained from 3 subjects was analyzed by SDS PAGE and silver staining (FIG. 2), and found to consistently have two low molecular weight bands of approximately 8–12,000 kDa. After baseline spirometery measurements, subjects inhaled 5 breaths of saline using a DeVilbis nebulizer hooked up to a Rosenthal-French dosimeter and compressed air. Repeat spirometric measurements were taken, then 5 breaths of ARF were administered every 5 minutes, beginning with a 1/10,000 dilution and progressing to a 1/10 dilution (equal to undiluted platelet supernatant) which was administered as 10 breaths. Future inhalation of ARF can be carried out using hand held metered dose inhalers or hand held inhalers in which lyophilized ARF is mixed with lactose in a capsule and the powder generated by the force of inspiration.

EXAMPLE 15

Results of Administration of ARF to Humans

Figure 8:
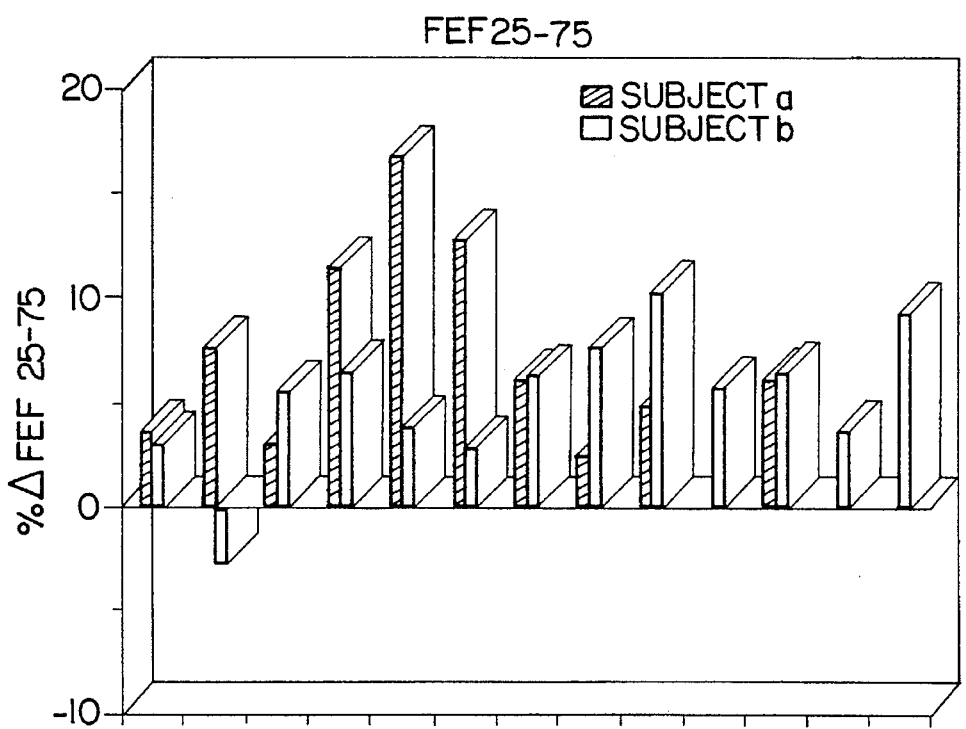
FIG. 8 is a plot of $FEF_{25-75}$ over time post-inhalation. Bars represent individual measurements which were obtained at 5, 15, and 30 minutes, and then hourly from hours 1–6. Subject A also had a measurement at 8 hours, while B was additionally studied at 7, 8, 24, and 48 hours. Percentage change is calculated from values obtained after saline inhalation and values obtained post-ARF administration. ARF inhalation in the first 2 volunteers resulted in a rapid improvement of $FEF_{25-75}$.
Figure 9:
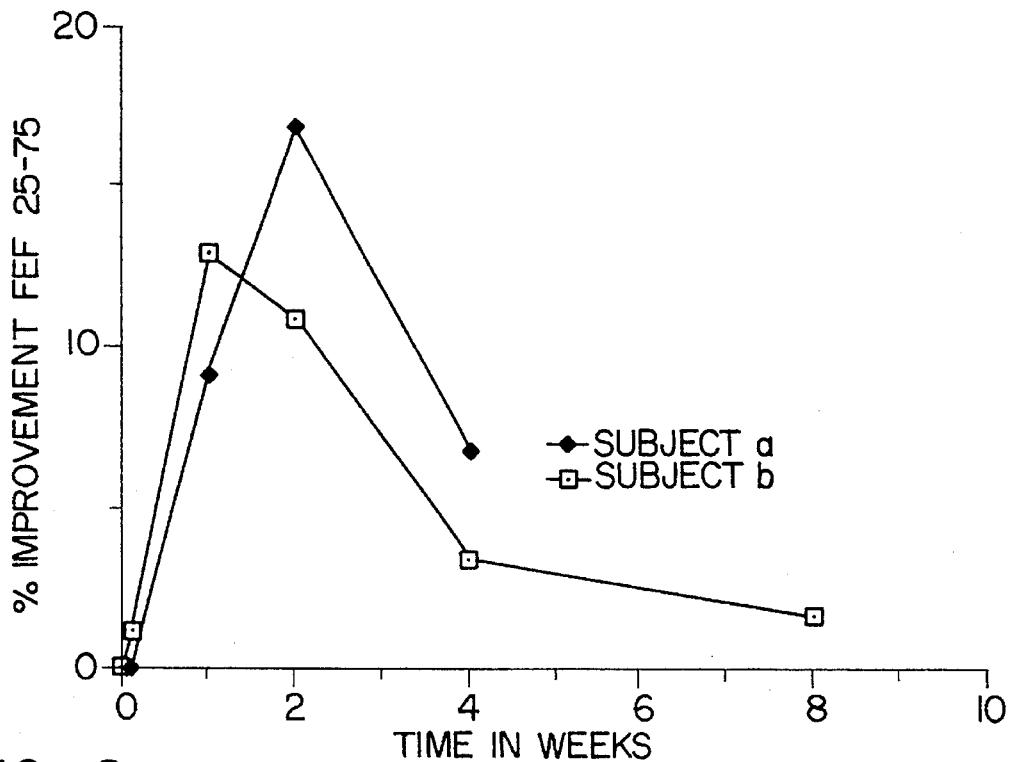
FIG. 9 is a plot of the improvement of $FEF_{25-75}$ over time in human subjects after a single inhalation of ARF.
Figure 10:
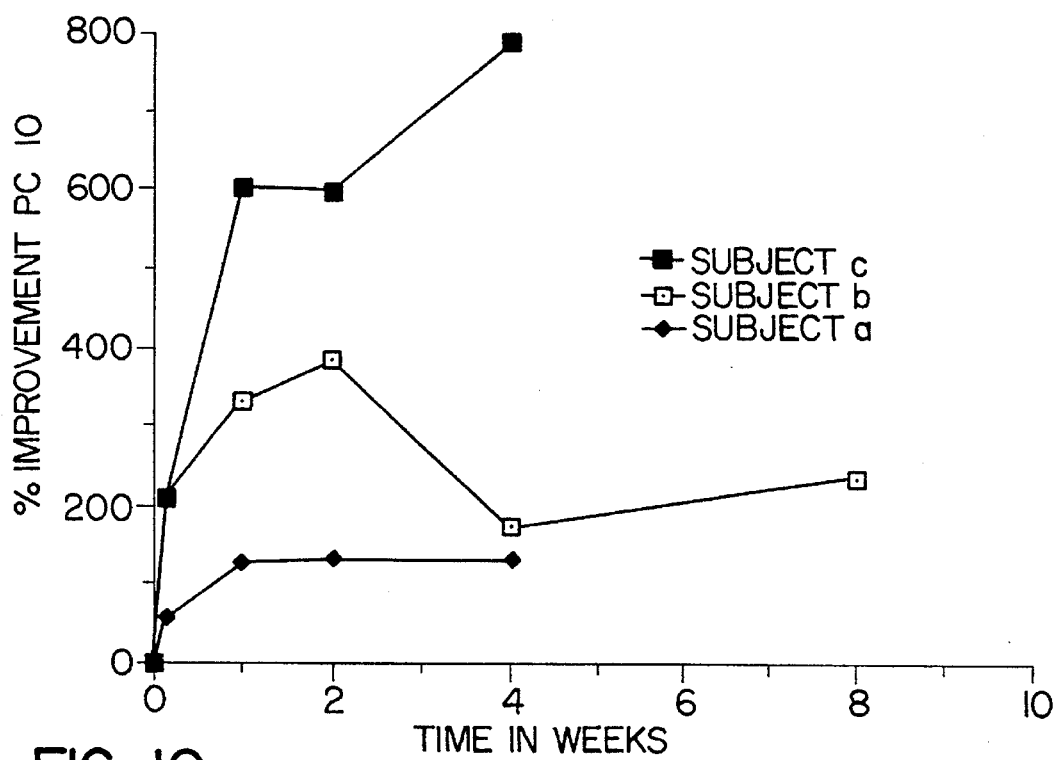
FIG. 10 is a plot of the improvement in $PC_{10}$ as a function of time after a single inhalation of ARF. Values are obtained by comparison of post-inhalation values with baseline values obtained after saline inhalation and prior to ARF treatment. A single inhalation challenge with ARF results in prolonged improvement of hyperresponsiveness. The effect peaks at 1–2 weeks but persists for months. Subjects a and b no longer had measurable $PC_{20}$'s.

ARF challenge results in a modest though rapid and prolonged improvement in airflow, particularly in the smaller airways (as measured by the forced expiratory flow rate between 0.25 and 0.75 seconds of exhalation ($FEF_{25-75}$), FIGS. 8 and 9). The most dramatic effect of ARF inhalation is reduced reactivity to methacholine. As shown in FIG. 10, improvement is rapid and persists for weeks to months. In fact, for 2 of the first 3 subjects studied, $PC_{20}$'s were no longer attainable, and $PC_{10}$'s are therefore depicted. Subjects report improvement in symptoms, and 2 subjects have resumed jogging. One subjected noted that exercise-induced asthma was no longer present 48 hours after challenge, and failed to return after several months.

The preceding Examples are included for illustrative purposes only and are not intended to be construed as limiting the invention being defined by the following claims.

That which is claimed is:

1. A method of treating asthma in a subject in need of such treatment, comprising contacting an effective asthma-combating amount of Asthma Reversal Factor (ARF) to the respiratory epithelium of said subject.

2. A method according to claim 1, wherein said ARF is carried by a pharmaceutically acceptable carrier.

3. A method according to claim 1, wherein said ARF is carried by a pharmaceutically acceptable liquid carrier.

4. A method according to claim 1, wherein said ARF is administered to said subject in an amount ranging from 0.1 nanograms to 10 micrograms.

5. A method according to claim 1, wherein said ARF is administered to said subject in an amount ranging from 1 nanogram to 1 microgram.

6. A method according to claim 1, wherein said asthma reversal factor is glycosylated.

7. A method of treating asthma in a subject in need of such treatment, comprising administering to the subject by inhalation respirable particles comprising *Asthma Reversal Factor (ARF)*, administered in an effective asthma-combating amount.

8. A method according to claim 7, wherein said respirable particles are liquid particles.

9. A method according to claim 7, wherein said respirable particles are solid particles.

10. A method according to claim 8, wherein said ARF is administered to said subject in an amount ranging from 0.1 nanograms to 10 micrograms.

11. A method according to claim 7, wherein said ARF is administered to said subject in an amount ranging from 1 nanogram to 1 microgram.

12. A method according to claim 7, wherein the asthma reversal factor is glycosylated.

\* \* \* \* \*